(12) United States Patent
Kil

(10) Patent No.: US 7,967,731 B2
(45) Date of Patent: Jun. 28, 2011

(54) SYSTEM AND METHOD FOR MOTIVATING USERS TO IMPROVE THEIR WELLNESS

(75) Inventor: David H. Kil, Santa Clara, CA (US)

(73) Assignee: SK Telecom Americas, Inc., Sunnyvale, CA (US)

( * ) Notice: Subject to any disclaimer, the term of this patent is extended or adjusted under 35 U.S.C. 154(b) by 0 days.

(21) Appl. No.: 12/791,799

(22) Filed: Jun. 1, 2010

(65) Prior Publication Data

US 2010/0331146 A1 Dec. 30, 2010

Related U.S. Application Data

(60) Provisional application No. 61/182,674, filed on May 29, 2009.

(51) Int. Cl.
*A63B 71/00* (2006.01)
(52) U.S. Cl. .............. 482/8; 482/1; 482/9; 482/901; 600/300
(58) Field of Classification Search ............ 482/1–9, 482/900–90; 434/247; 601/23; 600/300
See application file for complete search history.

(56) References Cited

U.S. PATENT DOCUMENTS

| | | | |
|---|---|---|---|
| 6,827,670 B1 * | 12/2004 | Stark et al. ............... | 482/9 |
| 2001/0039503 A1 | 11/2001 | Chan et al. | |
| 2005/0240544 A1 | 10/2005 | Kil et al. | |
| 2006/0089542 A1 * | 4/2006 | Sands ................. | 600/300 |
| 2007/0122780 A1 | 5/2007 | Moon et al. | |
| 2008/0076637 A1 | 3/2008 | Gilley et al. | |
| 2008/0076972 A1 | 3/2008 | Dorogusker et al. | |
| 2008/0077619 A1 | 3/2008 | Gilley et al. | |
| 2008/0077620 A1 | 3/2008 | Gilley et al. | |
| 2008/0077881 A1 | 3/2008 | Gilley et al. | |
| 2008/0096726 A1 | 4/2008 | Riley et al. | |
| 2008/0294013 A1 | 11/2008 | Gobeyn et al. | |
| 2009/0054743 A1 | 2/2009 | Stewart | |
| 2010/0228076 A1 * | 9/2010 | Blank et al. .......... | 600/18 |

OTHER PUBLICATIONS

Christian K. Roberts and R. James Barnard, "Effects of exercise and diet on chronic disease," J. Appl. Physiology, vol. 98, No. 3, pp. 3-30, 2005.
Honghong Zhou et al., "A Computer Simulation of Model of Diabetes Progression, Quality of Life, and Cost," Diabetes Care, vol. 28, No. 12, pp. 2856-2863, Dec. 2005.
David M. Eddy and Leonard Schlessinger, "Archimedes: A trial-validated model of diabetes," Diabetes Care, vol. 26, No. 11, pp. 3093-3101, Nov. 2003.
Rete algorithm, http://en.wikipedia.org/wiki/Rete_algorithm, Wikipedia, accessed in May 2009.
Paul R. Rosenbaum and Donald B. Rubin "The central role of the propensity score in observational studies for causal effects," Biometrika 70, p. 41-55, 1983, Great Britain.

* cited by examiner

*Primary Examiner* — Glenn Richman
(74) *Attorney, Agent, or Firm* — Thomas Ham; Wilson & Ham

(57) ABSTRACT

A system and method for motivating users to improve their wellness utilizes complex event processing on sensor and user-interaction data of the users collected over time using inference and predictive models in order to deliver personalized interactions to motive the users toward their wellness goals.

20 Claims, 12 Drawing Sheets

SYSTEM AND METHOD FOR MOTIVATING USERS TO IMPROVE THEIR WELLNESS

CROSS REFERENCE TO RELATED APPLICATION

This application is entitled to the benefit of U.S. Provisional Patent Application Ser. No. 61/182,674, filed on May 29, 2009, which is incorporated herein by reference.

BACKGROUND OF THE INVENTION

Obesity has become a global epidemic affecting over two-thirds of the U.S. population. Obesity leads to dramatically increased risks for various chronic illnesses, such as diabetes, heart disease, and even certain types of cancer. It has been estimated that up to seventy five percent of chronic illnesses can be prevented or moderated through lifestyle changes. In particular, exercise and diet can be effective in improving population health, even for those with chronic conditions. However, seemingly simple tasks, such as walking a couple of miles a day and eating right, have been a huge challenge for most people, as evident by the obesity epidemic in U.S.

Therefore, there is a need for a system and method to motivate individuals to make proper lifestyle changes to improve their health.

SUMMARY OF THE INVENTION

A system and method for motivating users to improve their wellness utilizes complex event processing on sensor and user-interaction data of the users collected over time using inference and predictive models in order to deliver personalized interactions to motive the users toward their wellness goals.

In an embodiment, a method for motivating users to improve their wellness comprising receiving sensor data and user-interaction data of a user at a system, the sensor data including information electronically sensed from one or more sensors, the user-interaction data including information derived from interactions between the user and the system and between the user and others in the system, performing continuous analytics on the received sensor and user-interaction data over time to determine current and predicted future wellness states of the user using complex event processing with inference and predictive models, performing background analytics on the received sensor and user-interaction data along with previously received sensor and user-interaction data for the user and other users to update parameters of the inference and predictive models, generating a personalized intervention for the user using at least the determined current and predicted future wellness states when a triggering rule is satisfied to motivate the user toward a wellness goal of the user, and performing outcomes analytics to investigate which interventions work for which users in order to optimize interventions over time.

In an embodiment, a system for motivating users to improve their wellness comprises a continuous analytics module, a background analytics module, an intervention module and an outcomes analytics module. The continuous analytics module is configured to perform continuous analytics on sensor and user-interaction of a user data over time to determine current and predicted future wellness states of the user using complex event processing with inference and predictive models. The sensor data includes information electronically sensed from one or more sensors. The user-interaction data includes information derived from interactions between the user and the system and between the user and others in the system. The background analytics module is configured to perform background analytics on the received sensor and user-interaction data along with previously received sensor and user-interaction data for the user and other users to update parameters of the inference and predictive models. The intervention module is configured to generate a personalized intervention for the user using at least the determined current and predicted future wellness states when a triggering rule is satisfied to motivate the user toward a wellness goal of the user. The outcomes analytics module is configured to perform outcomes analytics to investigate which interventions work for which users in order to optimize interventions over time.

Other aspects and advantages of the present invention will become apparent from the following detailed description, taken in conjunction with the accompanying drawings, illustrated by way of example of the principles of the invention.

DETAILED DESCRIPTION

Figure 1:
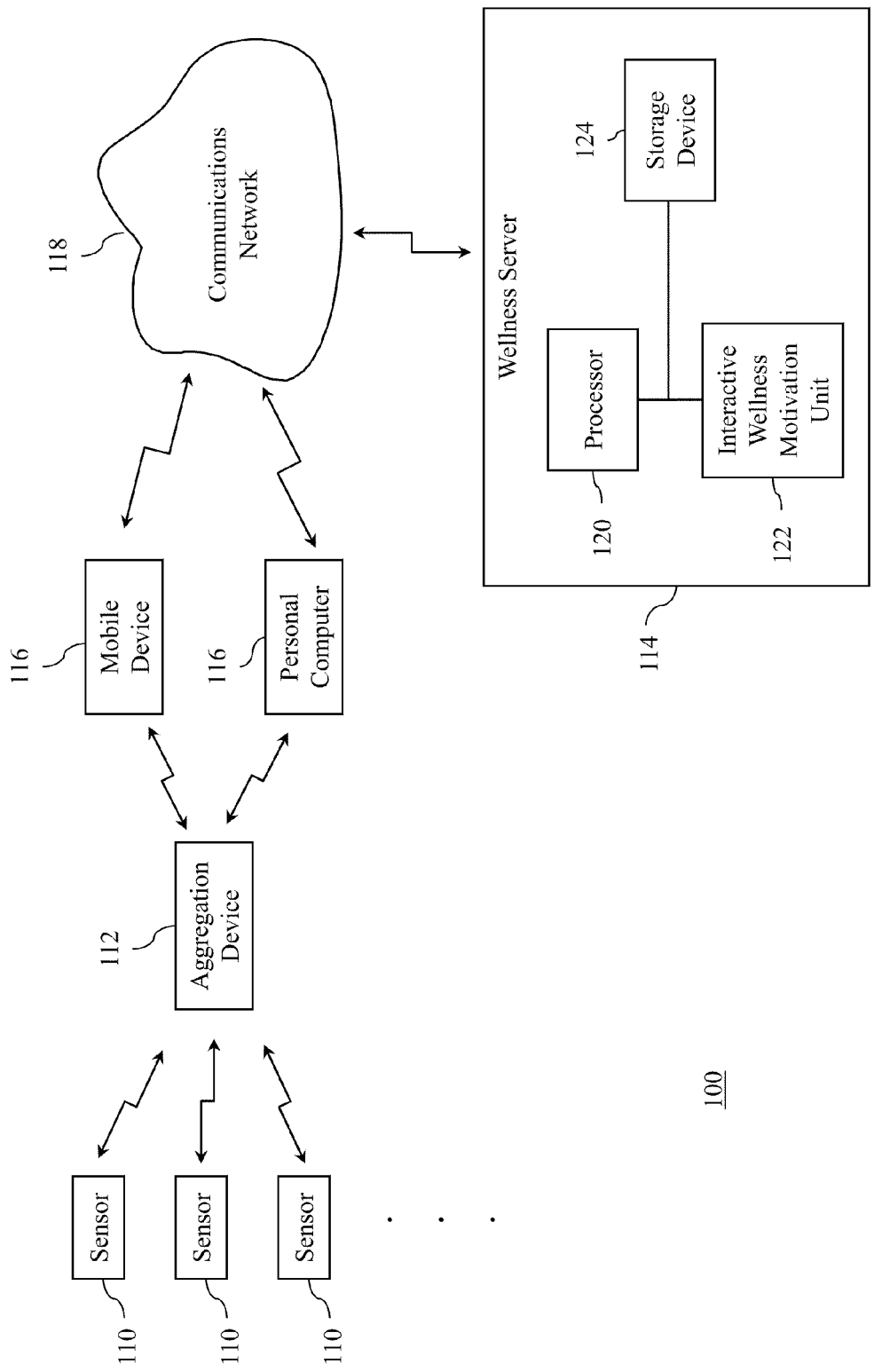
FIG. 1 is a block diagram of a system for motivating users to improve their wellness in accordance with an embodiment of the invention.

With reference to FIG. 1, a system 100 for motivating users to improve their wellness in accordance with an embodiment of the invention is described. The system is designed to take users on a fun-filled journey of self-discovery consisting of multiple connected small journeys. Self-discovery encompasses (1) learning about causal relationships between lifestyle choices and mind-body health, (2) understanding what keeps them motivated to be able to sustain healthy living on their own, consistent with a goal of teaching them how to fish, not just give them fish, and (3) becoming health and wellness advocates. As described in more detail below, the system uses a cloud informatics platform that works in concert with sensors and communications networks in order to engage and motivate users to improve wellness and stay healthy. The platform processes sensor and user-interaction data to understand each individual dynamically so that the system can guide each user towards a highly personalized and rewarding wellness trajectory. The platform can also leverage an automatically reconfigurable and continuously adaptive suite of user experience analytics functions to coddle, encourage, challenge and entertain each user throughout connected journeys of self-discovery and learning in individual and social settings.

In an embodiment, the system 100 operates in a closed-loop framework, which includes four steps that are repeated with the system becoming smarter as the cycle continues. At step 1, user data is collected unobtrusively as a foundation of ambient intelligence. This step involves seamless aggregation and transformation of heterogeneous user data with focus on user privacy protection. At step 2, informatics is designed to prescribe proactive, personalized, motivational interventions on demand. This step involves identification of population micro-segments for virtual coating and guidance using, for example, predictive modeling, inference engine, context-aware considerate computing and/or complex event processing. At step 3, users are engaged and motivated individually and in a social context. This step involves using portals, avatars, games, fun messaging, leaning and social networks to create sustainable user health behavior change. At step 4, an analytics process is performed. This analytics process includes (1) segmenting users rapidly using real-time, inferred feedback and predicted user states, (2) predicting the most effective intervention for each group, (3) determining efficacy rates for delivered interventions, and (4) incorporating learning into a closed-loop process. The most importance aspect of this process is that by using the latest Integrated Communications Technologies (ICT), the process can be executed faster over a broader population set at much lower cost. This last step involves learning what works and what doesn't work for which user segments, and adapting system operations automatically.

As illustrated in FIG. 1, the system 100 includes one or more sensors 110, a data aggregation device 112 and a wellness server 114, which may be implemented as one or more servers. The sensors and the data aggregation device are used to collect raw data of the users of the system 100 over time, such as activity data, fitness data, and biometric parameters and biomarkers. These sensors are configured to electronically measure or sense physical activities, biometric parameters and biomarkers. As an example, the sensors may be implemented as or part of a pedometer, an exercise equipment (e.g., a treadmill), a weight scale, a height measuring device, a blood pressure measuring device, a pulse rate sensing device, a total cholesterol measuring device, an HDL/LDL measuring device, a triglyceride measuring device, a blood glucose measuring device, and other type of a medical measuring device.

The data aggregation device 112 is an electronic device that is configured to receive and aggregate the data from the sensors 110 via wireless or wired connections to be transmitted to the wellness server 114. The data aggregation device may transmit the data to the wellness server either directly or indirectly via a computing device 116 (e.g., a mobile device or a personal computer) through a network 118, such as the Internet using a portal, such as a web portal 126 or a mobile portal 128 (shown in FIG. 2), provided by the wellness server. In an embodiment, the data aggregation device may be configured to function as one or more sensors to also measure or sense one or more physical activities, biometric parameters and biomarkers of a user. As an example, the data aggregation device may be configured to function as a pedometer using a 3-axis accelerometer.

Other types of data are also transmitted to the wellness server 114. These other types of data include user interactions between a user and the system 100 and between the user and others in the system. These user-interaction data may include questions and answers, social networking, games and other interactive interactions, as well as other interaction data as described below.

As illustrated in FIG. 1, the wellness server 114 includes a processor 120, an interactive wellness motivation unit 122 and a storage device 124. Although only a single processor and a single storage device are illustrated in FIG. 1, the wellness server may include multiple processors and/or multiple storage devices, which may be distributed in a network of servers. In general, the interactive wellness motivation unit is designed to uncover interesting relationships automatically, looks for moments of user engagement, deliver the right intervention to the right user at the right time, and adapt system parameters to changing preferences of and contexts around users based on the amount of impact or outcomes of such interventions.

In order to accomplish the above design goals, the interactive wellness motivation unit 122 is configured to (1) perform continuous analytics on the sensor and user-interaction data of users over time to determine current and predicted future wellness states of the users using complex event processing with inference and predictive models, (2) perform background analytics on the sensor and user-interaction data along with previously collected sensor and user-interaction data of the users to update parameters of the inference and predictive models, (3) generate personalized interventions for the users using at least the current and predicted future wellness states when one or more triggering rules are satisfied to motivate the users toward their wellness goals, and (4) perform outcomes analytics to investigate which interventions work for which users in order to optimize interventions over time. The interactive wellness motivation unit is also configured to perform other tasks to engage and motivate the users toward their wellness goals, as described in more detail below. The interactive wellness motivation unit may be implemented in any combination of hardware, firmware and software. Thus, the components of the wellness motivation unit may comprise specialized circuits and/or computer programs. In some embodiments, the interactive wellness motivation unit is entirely implemented as one or more algorithms in the form of computer programs that are executed by the processor 120.

The interactive wellness motivation unit 122 in accordance with an embodiment performs the following five tasks continuously to engage and motive the users toward their wellness goals:

Task 1—Creation of individually and socially linked events over time: These events include inferred and predicted user states by using inference and predictive models, such as dynamic Bayesian networks and nonparametric learning algorithms.

Task 2—Complex event processing: Linked events are passed through a rules management engine in real time, where recent events are compared to triggering rules (recent weight loss, altered substance use patterns, and low-mood selection) for micro-interventions (Careful, it may be especially important to use exercise to boost your mood these days.... Here is how others like you are staying on course). These rules are, in part, generated by domain experts initially, and then dynamically "machine-learned" from growing volumes of historical data.

Task 3—User experience optimization: This engine handles all user touch-points. For example, soliciting additional information in a few brief questions might improve the quality and impact of a given micro-intervention. This engine asks the right questions in a considerate manner, fine tunes micro-interventions with this extra bit of information, and delivers the interventions at the right time to the right user in the right context.

Task 4—Broadband outcomes analytics: This is where the effectiveness of multiple simultaneous and staggered interventions is evaluated as a function of user parameters and situational context.

Task 5—Continuous learning and track maintenance: The orchestration engine takes care of experimental design, embedding learning into the system, maintaining complex linkages of events over time and people (similar to multiple-target tracking used in military), and other overhead activities.

Figure 2:
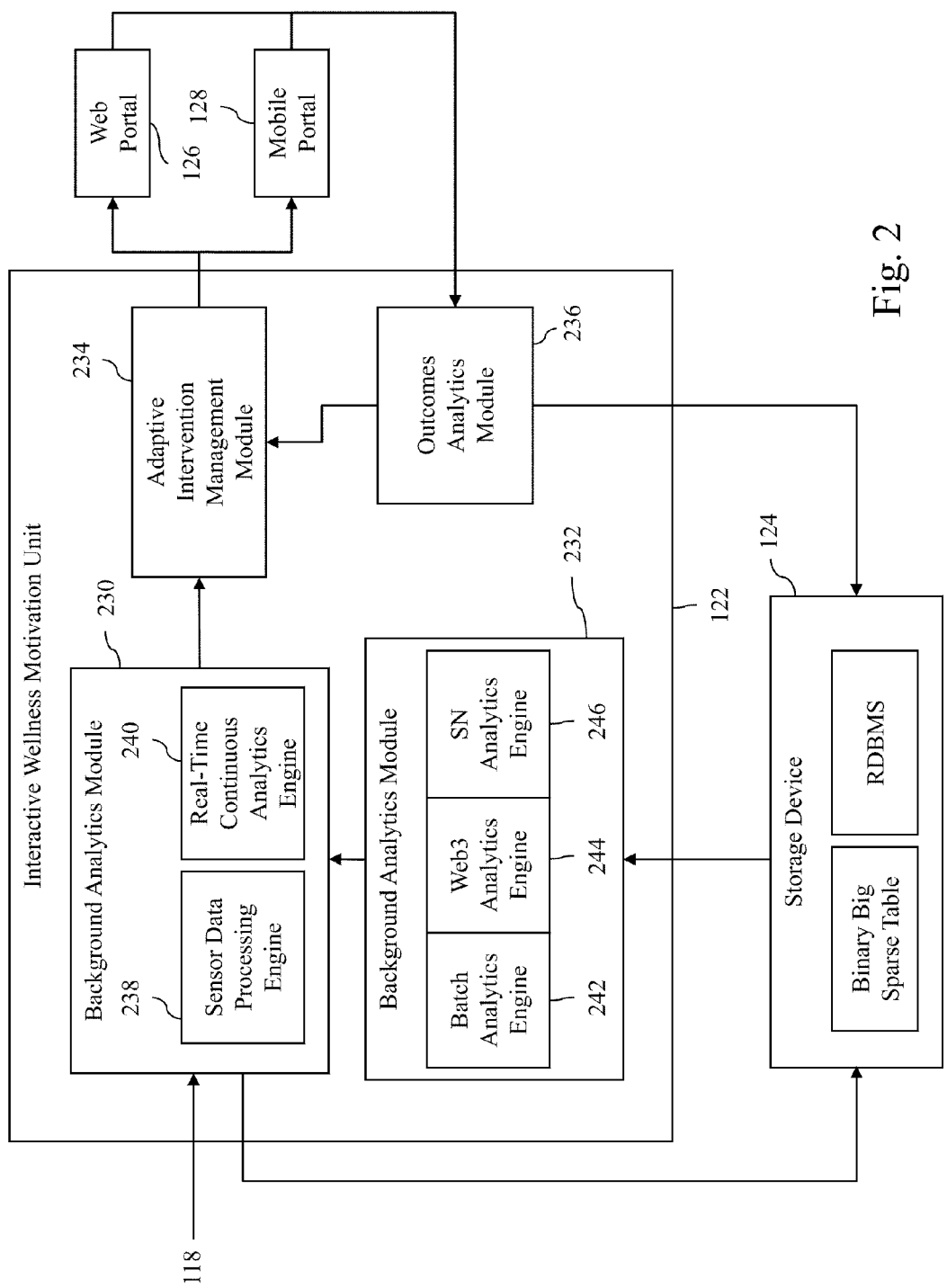
FIG. 2 is a block diagram of components of the system shown in FIG. 1 in accordance with an embodiment of the invention.

Turning now to FIG. 2, components of the interactive wellness motivation unit 122 in accordance with an embodiment of the invention are illustrated. As shown in FIG. 2, the interactive wellness motivation unit includes a continuous analytics module 230, a background analytics module 232, an adaptive intervention management (AIM) module 234 and an outcomes analytics module 236. The continuous analytics module is configured to perform continuous analytics on sensor and user-interaction data of users over time to determine current and predicted future wellness states of the users using complex event processing with inference and predictive models. In the illustrated embodiment, the continuous analytics module includes a sensor data processing engine 238 and a real-time continuous analytics engine 240. The background analytics module is configured to perform background analytics on the sensor and user-interaction data of the users along with previous sensor and user-interaction data of the users to update parameters of the inference and predictive models. In the illustrated embodiment, the background analytics module includes a batch analytics engine 242, a web3 analytics engine 244 and a social networking analytics engine 246. The AIM module is configured to generate a personalized intervention for the user using at least the determined current and predicted future wellness states when a triggering rule is satisfied to motivate the user toward a wellness goal of the user. The outcomes analytics module is configured to perform outcomes analytics to investigate which interventions work for which users in order to optimize interventions over time. These components of the interactive wellness motivation unit are configured to perform the above tasks as well as other tasks, which are described in more detail below. As noted above, these components of the interactive wellness motivation unit may be implemented in any combination of hardware, firmware and software, and some or all may comprise specialized circuits and/or computer programs. In some embodiments, each of these components may be entirely implemented as one or more algorithms in the form of computer programs that are executed by the processor 120.

Inputs to the interactive wellness motivation unit 122 consist of one or more of the following data:
1. Streaming activity tracker data
2. Transactional biomarker data, such as weight, body fat percentage, blood pressure, pulse rate, lab-on-a-chip data for blood chemistry analysis, etc.
3. Self-reported data from Health Fun Assessment (HFA) specially designed to minimize user irritability and maximize prediction power using advanced analytics: HFA is to be taken over several days with questions being asked in a context-dependent way for maximum response rate.
4. Context-dependent Ecological Momentary Assessment (EMA) data
5. user interaction data through H-Pod, mobile, and Web portals
6. Web 3.0 sensor data including text, cartoon, picture, audio, and video files
7. Proprietary content created to integrate various multimedia content into a pithy and impactful feedback
8. User-generated content including motivational stories and event-triggered micro-intervention content
9. Consumer behavioral marketing (CBM) data These inputs are processed in a manner that focuses on how to create a sustainable behavior change with gentle nudging by tying lifestyle choices to causal outcomes in mind and body. Nudging is consistent with key principles of choice architecture, where situation-dependent and tailored interventions are not overbearing, but conceptually similar to the best friend's coaching that focuses on the positives. The different components of the interactive wellness motivation unit 122 are described in the following process flow description in accordance with an embodiment of the invention.

Let $x_{sensor}(t)$ represent various input data as a function of time, where sensor $\epsilon$ {activity, biomarker, HFA, EMA, interaction, web3, content, CBM}. The first task is to put all the input data into a multidimensional, time-synchronized, sparse array S(t, T (sensor), n), where n is the user index and the T(•) operator denotes the transformation of $x_{sub}(t)$ through a variety of digital signal processing and statistical trending algorithms. The sensor data processing engine is configured to perform T(•) operations. Here are examples of T(•) operations that can be performed by the sensor data processing engine 238 of the continuous analytics module 230.
1. Linear regression to estimate trend.
2. Polynomial regression of order two to detect convex and concave patterns
3. Any spectral or scale transform to detect the cyclicality of activities and identify signal building blocks.
4. Aggregation operators.
5. Mathematical operators for statistical characterization, such as moments, probability distributions, and linear/nonlinear models.
6. Windowing operations (timeframe, overlap).
7. Concept of states and state evolutions that span multiple timeframes.
8. Time-lagged associations between events, such as full activity at t−1 and improving biomarkers at t.
9. An embedded phase map that shows event trajectories, such as a compressed (through principal component analysis) map of x(t) vs. x(t−1) vs. . . . vs. x(t−N−1), where N is the embedding dimension.
10. Nonlinear or continuous-density discretization of continuous inputs with saturation for modeling with discrete-node Bayesian networks.

The sensor data processing engine 238 transforms $x_{sensor}$(t) into S(t, T (sensor), n), which is then stored in the storage device 124 for continuous or real-time analytics and in Big Binary Table (BBT) or Enterprise Data Warehouse (EDW) for background analytics on historical data (i.e., previously received sensor and user-interaction data)—Web3, social networking, and batch analytics.

The real-time continuous analytics engine 240 of the continuous analytics module 230 is configured to perform four tasks—(1) inference of concurrent, unknown variables from instantiated ones, (2) prediction of future states of variables of interest, such as weight and activity, (3) appending inferred and predicted metadata to S(t, T (sensor), n), and (4) pattern matching of current events with stored complex-event triggers that require interventions. The appending of predictive-model outputs is important in devising proactive interventions based on likely future events, not what has already taken place in the past.

The pattern matching of current events against the stored complex-event triggers is conceptually similar to, but more efficient than, the Rete algorithm designed by Charles Forgy. The entire complex event (CE) trigger database is encoded into a sparse matrix consisting of columns corresponding to rules attributes, instantiated by discretized values for operands and operators.

Parameters of predictive and inference models are updated and instantiated from the batch analytics engine 242 of the background analytics module 232. The complex-event triggers are generated either automatically from various predictive models or via user-provided rules using the business rules management system. Predictive models are designed to predict events out of norm (i.e., weight increase or decrease beyond normal fluctuations, significant departure from normal activity patterns) with enough time to devise and administer proactive interventions.

The batch analytics engine 242 has a built-in algorithm that selects the right learning algorithms based on the actual probability distribution of good features and the nature of relationships between good features and dependent variables. The batch analytics engine has a history of model performances and metadata about good features, where features are ranked based on multidimensional combinatorial optimization. The combinatorial optimization facilitates the finding of the minimum feature dimension for robustness and modeling accuracy along the concept of the Bayesian Information Criterion. The batch analytics library, which can be stored in the storage device 124, includes a number of preprocessing algorithms, feature extraction routines, and learning algorithms in regression, classification, and Bayesian networks.

Figure 3:
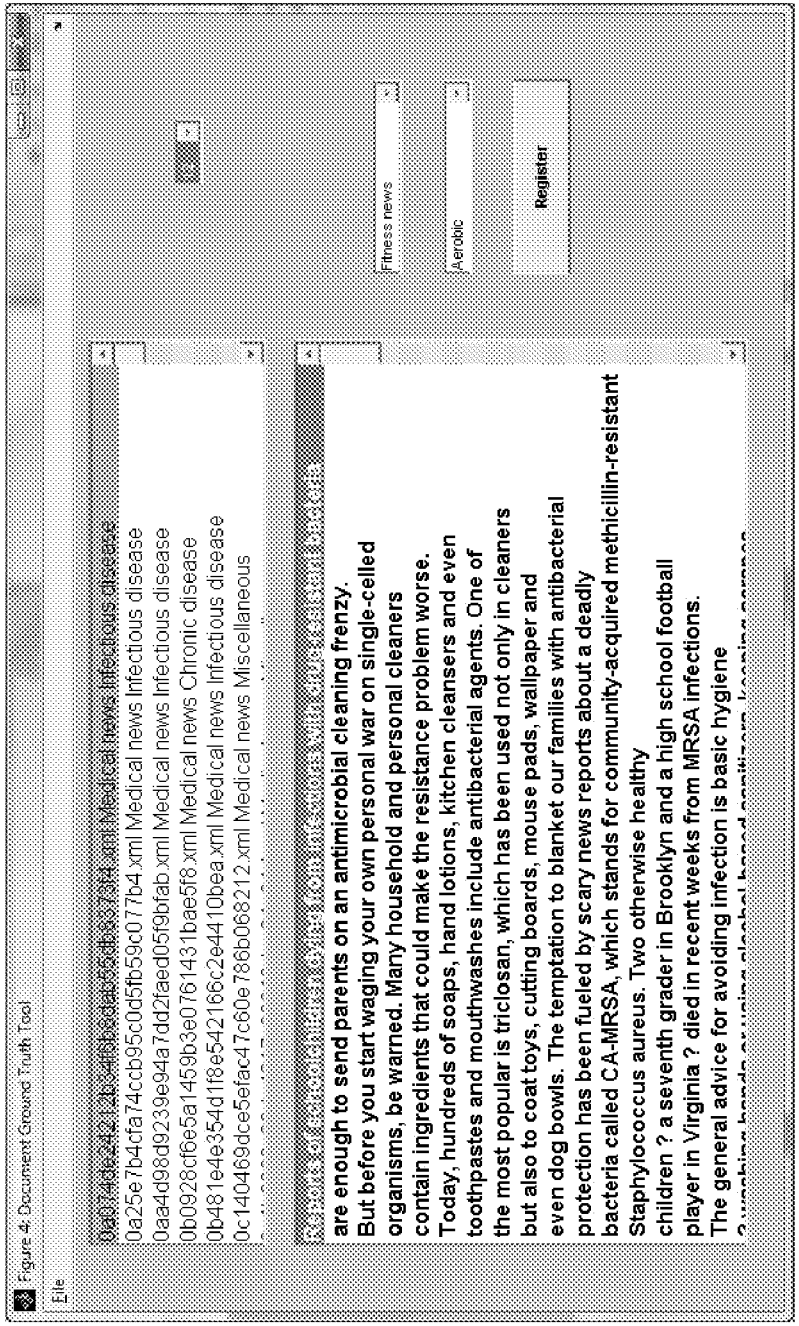
FIG. 3 illustrates an example of a Graphical User Interface (GUI) tool to create a supervised training set for preprocessing a document in accordance with an embodiment of the invention.
Figure 4:
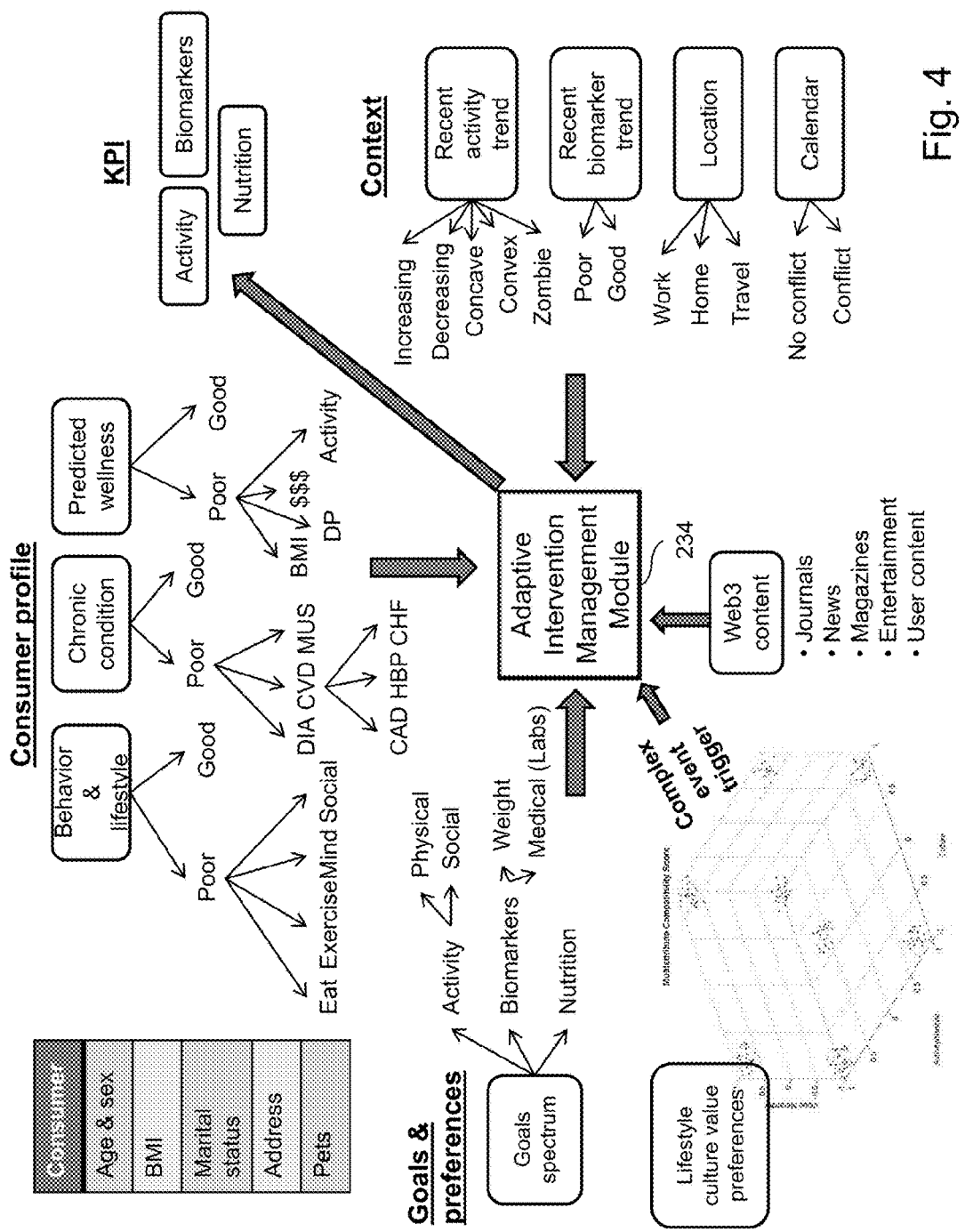
FIG. 4 illustrates hierarchical relationships of complex-event trigger, context, user profile, and goals/preferences in accordance with an embodiment of the invention.

The web3 analytics engine 244 of the background analytics module 232 is configured to perform one or more of the following tasks. The web3 analytics engine can be configured to extract documents or other content from various Web3 sensor sites, such as health/fitness/nutrition magazines, wellness-focused Web sites, medical journals, health-news Web sites, health-entertainment sites, and motivational-content sites. The web3 analytics engine can also be configured to preprocess each document. Preprocessing a document may involve using a Graphical User Interface (GUI) tool to create a supervised training set. An example of a GUI tool in accordance with an embodiment of the invention is illustrated in FIG. 3. In FIG. 3, the illustrated GUI tool is a tool to provide truth data for semi-supervised training as part of active learning (to be used later during the actual preprocessing of documents). Preprocessing may also involve tokenization (i.e., dividing documents into words and word combinations that occur frequently), part-of-speech tagging, removing stop words (non-significant words, such as "the" "a" etc.), transforming words into their word stem including plurals, combining synonyms for feature-dimension reduction, looking for bigram and trigram words along with their frequencies and, from training data, looking for intersections of words from documents of different categories/sub-categories to create word-list filters or morphologies for specific categories and sub-categories. The web3 analytics engine can also be configured to extract features from each document. Features encompass (a) term frequency (TF)-inverse document frequency (IDF), (b) morphology (including bigrams and trigrams) filter outputs for specific topics or sentiments of interest, which are conceptually similar to spectral analysis of time-series sensor data, and (c) linguistic rules. The features can be encoded in a sparse matrix. The web3 analytics engine can also be configured to use Singular Value Decomposition (SVD) for further feature-dimension reduction over multiple documents, which can be used in latent semantic indexing. The web3 analytics engine can also be configured to append the category and sub-category labels to the compressed sparse feature matrix. The web3 analytics engine can also be configured to train learning algorithms to categorize, retrieve information from each document, and compute document-similarity coefficients. The web3 analytics engine can also be configured to use active learning and co-training to extend training to both labeled and unlabeled data sets. The web3 analytics engine can also be configured to map each processed document into complex-event triggers with ancillary user information consisting of profile, goals/preferences, and context. This step will produce a set of Web3 content that can be embedded into multimedia feedback to be constructed on the fly during runtime as a function of complex-event trigger, context, user profile, and goals/preferences. FIG. 4 shows the hierarchical relationships of these entities. FIG. 4 will be described in more detail below with reference to the AIM module 234.

Figure 5:
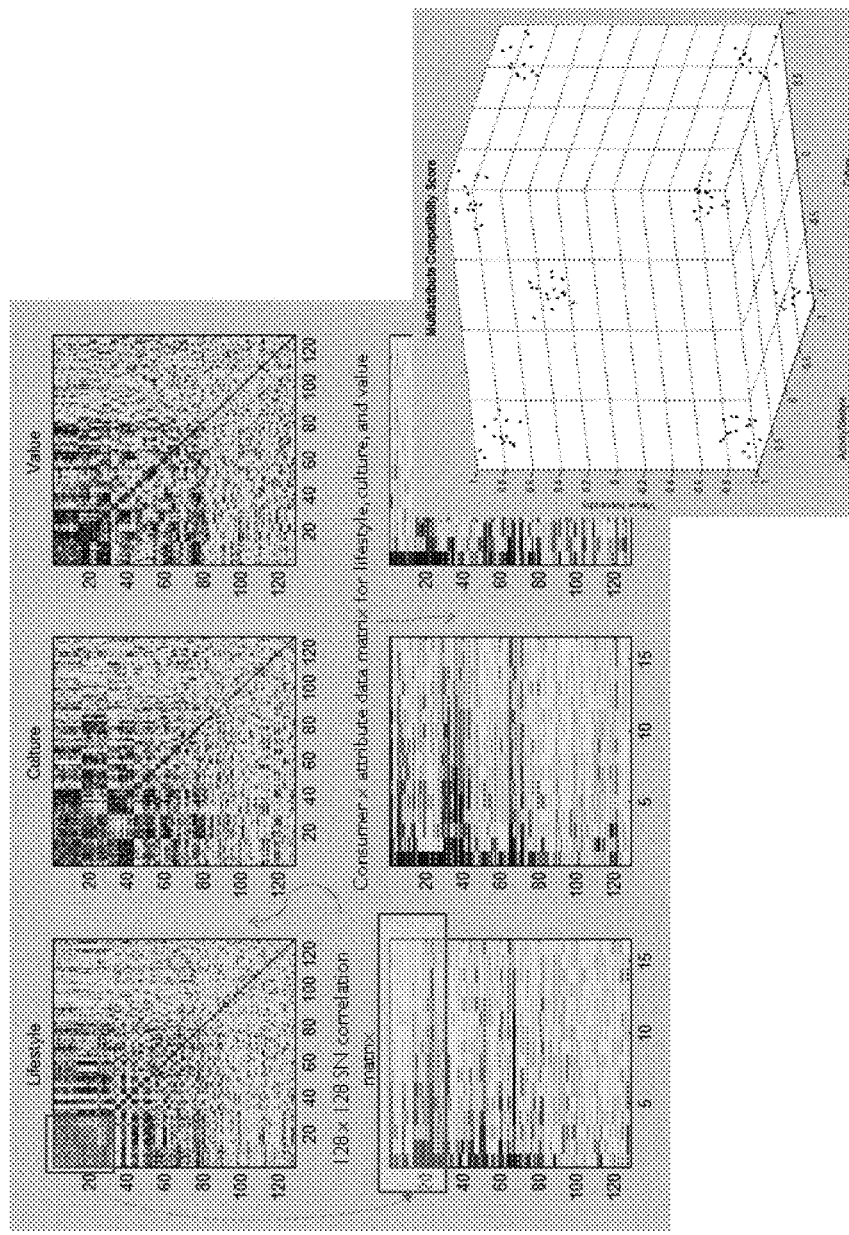
FIG. 5 illustrates the creation of social networks based on lifestyle, culture, and value attributes and displaying people with similar or opposite compatibility scores in the three dimensions in accordance with an embodiment of the invention.
Figure 6:
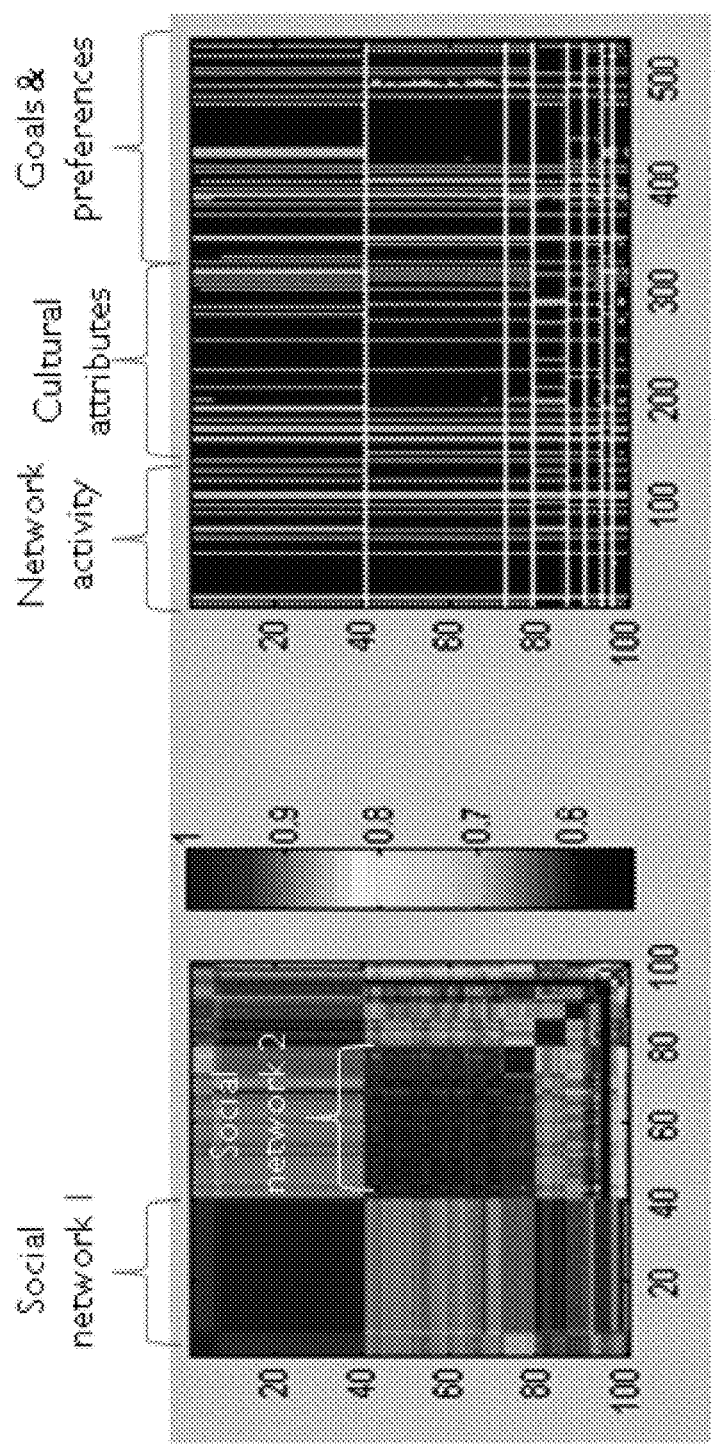
FIG. 6 illustrates the creation of multiple (2 large) ad hoc social networks based on parameters derived from social network activities, cultural attributes, goals, and preferences in accordance with an embodiment of the invention.
Figure 7:
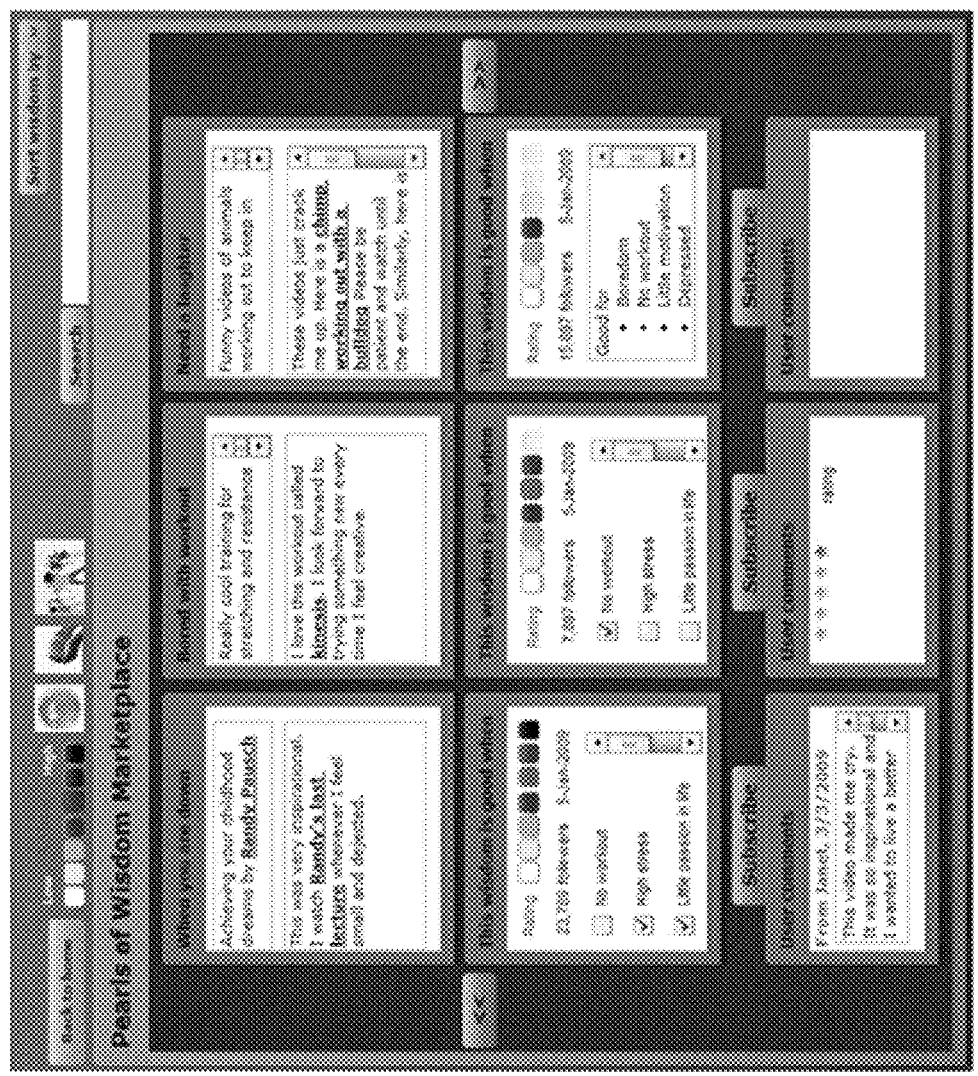
FIG. 7 illustrates an example of a motivational marketplace, where people can publish motivational content and specify situations and contexts under which such motivational content has been useful, in accordance with an embodiment of the invention.
Figure 8:
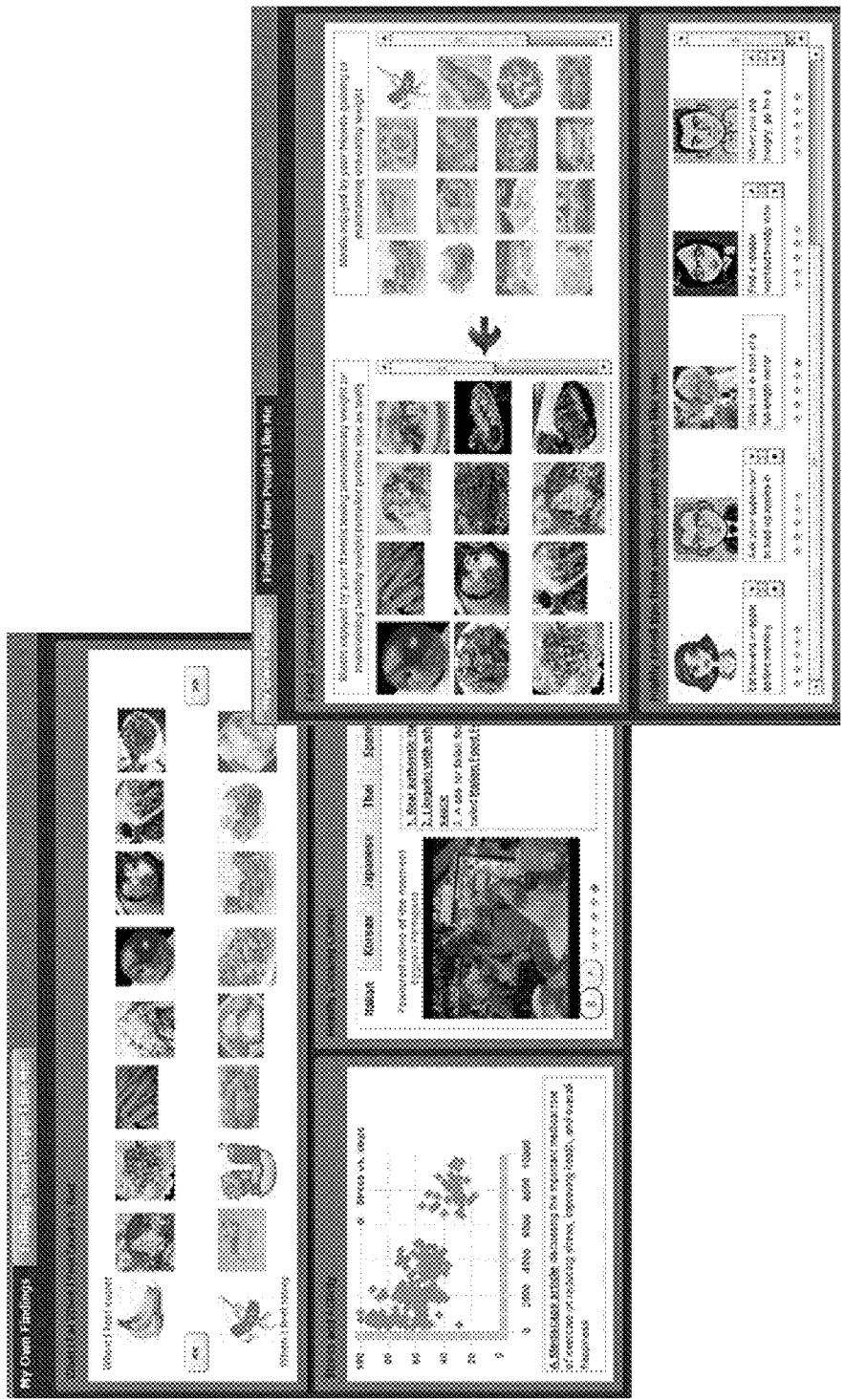
FIG. 8 illustrates an example of social nudging by comparing and contrasting what healthy and unhealthy people eat in accordance with an embodiment of the invention.

The social networking analytics engine 246 of the background analytics module 232 is configured to perform one or more the below-described tasks. The social networking analytics engine can score user along cultural-, lifestyle-, and value-compatibility dimensions, which can include creation of virtual social friends and coach-student relationships based on partial compatibility scores in an opt-in model (i.e., the user wants to meet virtually someone with similar cultural and value scores, but completely opposite in lifestyle to experience what the user is missing) and creation of virtual competition in individual and team sports as in Massively Multiplayer Online Role-Playing Games (MMORPG). The social networking analytics engine can provide fun voyeurism that allows the user to peek into the lives of people similar to or different from the user in the following areas:

1. Activities and hobbies that result in improved wellness as a personal challenge.
2. Encouragement by focusing on people doing worse than him, leveraging Daniel Gilbert's happiness theory.
3. Learning from others in fitness training, motivational strategies, fun activities while engaged in passive leisure, etc. FIG. 5 shows the creation of social networks based on lifestyle, culture, and value attributes and displaying people with similar or opposite compatibility scores in the three dimensions in accordance with an embodiment of the invention. Dynamic clustering of the person-lifestyle attribute data matrix leads to the creation of social-network clusters from which a scatter plot of multi-attribute compatibility scores can be generated. In FIG. 5, the first two clusters based on lifestyle (the first left column) show completely opposite characteristics as evidenced by the correlation and data matrices. The user can use a context menu to drill deeper into each of the 8 clusters to probe into their lifestyles, activities, and how they improve wellness.
4. Recommendation of Web3 content using multi-modal collaborative filtering with dynamic micro-segmentation of users while taking into account state transitions.
5. Real-time calculations of various composite scores and dynamic social networks.
   a. Determination of ad hoc social networks using various measures of similarity that people care about (the user would like to meet people with similar culture and goals, but with much better lifestyle than the user; the user would like to meet people the user can help and influence), as illustrated in FIG. 6, which shows the creation of multiple (2 large) ad hoc social networks based on parameters derived from social network activities, cultural attributes, goals, and preferences in accordance with an embodiment of the invention
   b. Calculate wellness scores based on behavior, lifestyle, chronic condition profile, and predicted future wellness/biometric states.
   c. Calculate reward points and unexpected gift items exploiting CF and outcomes analytics. Implement several flavors of rewards to learn which positive reinforcements lead to or can predict sustainable behavior change for various user clusters. This model is referred to herein as an adaptive rewards prediction algorithm.
   d. Social network (SN) influencers will be given reward points to distribute to their network members (e.g., 500 points with maximum of 100 pts per award and per person in 6 months). The awardees are free to spend points on any merchandise in the rewards network. The participating merchants are also encouraged to design a special discount program leveraging the adaptive rewards prediction algorithm. Influencers can use reward points to build even more influence and expand their networks.
6. User-generated content (UGC) marketplace: Create a marketplace where people can publish and subscribe to motivational content based on personal experiences. User ratings on and actual performances of people who subscribe to John's content constitute a subset of John's marketable social reputation. FIG. 7 shows a rendering of the motivational (Pearls of Wisdom) marketplace in accordance with an embodiment of the invention. In particular, FIG. 7 illustrates an example of a motivational marketplace, where people can publish motivational content and specify situations and contexts under which such motivational content has been useful. The UGC market place may include the following:
   a. Tools for publishing: The user can publish his or her motivational stories using a content-authoring tool with UI to specify event triggers and/or situational contexts under which the motivational stories were particularly useful.
   b. Subscription: Anyone can use a parameter- and text-driven search engine to find relevant and potentially useful motivational stories to which they can subscribe.
   c. Social reputation: In order to create a symbiotic relationship between subscribers and publishers, a user's social reputation is a nonlinear function of the quality and quantity of published content, the number of motivational stories and publishers the user subscribes to, and the number of subscribers, and the amount of impact on the subscribers.
7. Social rewards management: Rewards encompass multiple dimensions spanning both intrinsic and extrinsic motivators uncovered during registration and through observations.
   a. Wellness points: These points can be converted into merchandise in a virtual mall consisting of retailers looking for positive-sum user experience from those who need to upgrade image after losing weight, for example. Wellness points can be earned by improving fitness, winning in competitions or wagers, and being compliant with micro-interventions. That is, wellness points are earned based on individual efforts.
   b. Social reputation: Similar conceptually to player levels in computer games and belt hierarchy in martial arts. The user has to pass various thresholds in multiple dimensions to advance to different social reputation or influence levels. One's social reputation or influence is based on how others view, follow, and benefit from his contributions. Interestingly, when one's social reputation score reaches a certain level, the user will be given reward points that the user can distribute to the user's followers based on certain guidelines.
8. Social nudging and choice architecture: Instead of telling people what to do, gently suggest what healthy people are doing and eating. Furthermore, leverage the social causes that they believe in, such as green earth, green farming, favorite charities, and medical research, in order to get users to participate in competitions with pledges and wagers. FIG. 8 illustrates an example of social nudging by comparing and contrasting what healthy and unhealthy people eat in accordance with an embodiment of the invention. At an individual level, the interactive wellness motivation unit 122 shows relationships between stress and activity, contrasts food items consumed when feeling energetic and lethargic, displays relevant micro tips on how they stay fit and resist temptations from wellness gurus (those with high social reputation), and showcases recipes of healthy meals based on the user's cuisine interest.

The AIM module 234 designs and administers the most impactful real-time intervention. The inputs encompass a complex-event trigger, user profile, user goals and preferences, and context. Associated with each intervention is a set of outcomes or key performance indicators (KPI) that sheds light into whether or not the prescribed intervention has been effective. In an embodiment, the AIM module may be configured to solicit additional information in a few brief questions to improve the quality and impact of a given micro-intervention.

As shown in FIG. 4, the user profile is designed to be progressively hierarchical. One of the biggest challenges in personalized intervention design is the curse of dimensionality. The AIM module 234 copes with the challenge of combinatorial explosion by relying on the concepts of conditional independence, progressive intervention tailoring, marginal optimization, and entropy-based partitioning.

As illustrated in FIG. 4, the user's profile consists of three composite attributes—behavior/lifestyle score, chronic condition score, and predicted wellness score, which is estimated during real-time continuous analytics using instantiated parameters of a predictive model from the batch analytics engine 242. Each of these scores is based on a number of other user attributes.

For instance, the behavior/lifestyle (BL) score is parameterized as follows: $BL=\Sigma_{n=1}^{N}w_{n}\Gamma(x_{n})$, where N is the number of BL parameters, $w_n$ is the weight of the nth parameter, x is a BL parameter vector, and $\Gamma(\cdot)$ is a nonlinear operator. In general, $\Sigma_n w_n=1$. The BL score of poor can imply that the score is below the population mean. The BL parameter vector x could consist of eating habits self reported or estimated from scanned bar codes of grocery items or restaurant menu), exercise patterns inferred from an activity sensor, mind states derived from Ecological Momentary Assessment, and social activities based on online and real-world activities.

Marginal optimization means that instead of designing tailored intervention in the joint vector space, each variable can be assumed to be independent. The dimension-reduction factor is $K^N/_{(KN)}$, where K and N refer to the number of discrete components in each variable that spans the N-dimensional vector space.

Conditional independence is between marginal optimization and joint optimization. Conditional independence is the backbone of a causal Bayesian network. In essence, as many probabilistic nodes that do not have strong relationships with other nodes are decoupled such that the joint probability density function (PDF) can be constructed in a much simpler form with a much smaller number of parameters to be estimated.

Figure 9:
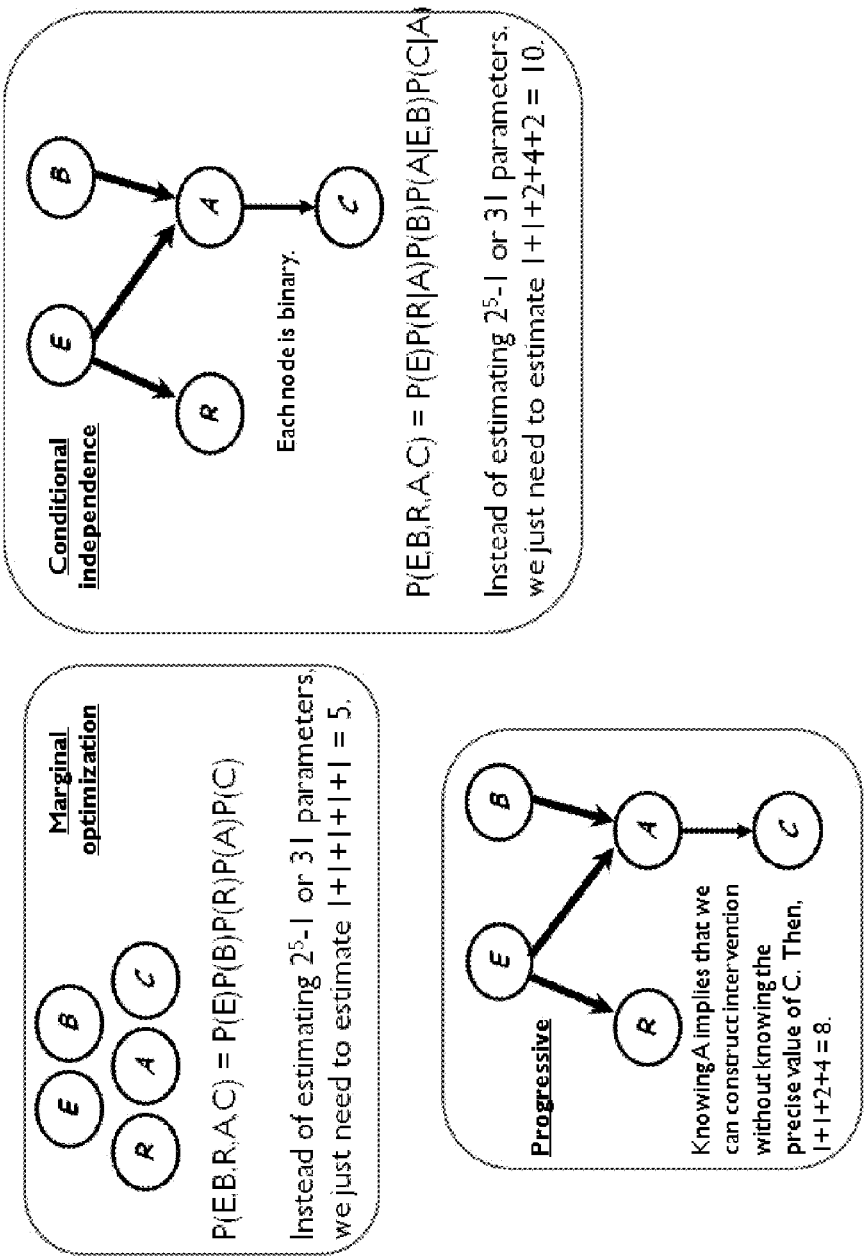
FIG. 9 illustrates three different algorithms to reduce the dimensionality of tailored-intervention design as part of scalable content building as a function of user profile, context, and goals in accordance with an embodiment of the invention.

Progressive-intervention tailoring leverages a hierarchical, variable-abstraction structure among nodes such that knowing a particular node's instantiation gives reasonable insights into its neighbors' inferred parameters. This allows construction of tailored intervention without knowing precisely the instantiated parameters of the neighboring nodes. FIG. 9 illustrates three different algorithms to reduce the dimensionality of tailored-intervention design as part of scalable content building as a function of user profile, context, and goals in accordance with an embodiment of the invention. The number of parameters to be estimated in based on an assumption that each vertex is a binary node. In the marginal optimization algorithm, $P(E,B,R,A,C)=P(E)*P(B)*P(R)*P(A)*P(C)$. In this algorithm, instead of estimating 25-1 or 31 parameters, only 1+1+1+1+1=5 parameters are estimated. In the conditional independence algorithm, $P(E,B,R,A,C)=P(E)*P(R|A)*P(B)*P(A|E,B)*P(C|A)$. In this algorithm, instead of estimating 25-1 or 31 parameters, only 1+1+2+4+2=10 parameters are estimated. In the progressive algorithm, $P(E,B,R,A,C)=P(E)*P(R|A)*P(B)*P(A|E,B)*P(C|A)$. In this algorithm, knowing A implies that intervention can be constructed without knowing the precise value of C. Thus, only 1+1+2+4=8 parameters are estimated.

The personalized micro-interventions provided by AIM module 234 can be multimedia feedbacks, which can include real-time content delivered via a mobile channel, comprehensive content delivered through a Web portal and an E-mail push channel or event-driven feedbacks based on complex-event triggers, on demand (user requests real-time information), and regular or irregular scheduled updates (once a day, for example). The personalized micro-interventions may be micro-interventions from friends or professional content creators, which can include messages generated by users for their friends or people who share high-compatibility scores, notes from physicians, nutritionists, and fitness trainers that can be delivered to their patients and clients based on complex-event triggers. The personalized micro-interventions may be recommended Web3 multimedia content, which can be sent via email or as content in a private inbox at the website provided by the wellness server 114 as URL or embedded video. The personalized micro-interventions can be event-driven user experience with visualization and virtual societies (e.g., a congratulatory message is sent that a user has lost weight. The message may include a graph of weight loss that is overlaid and a list of virtual societies that are similar in context with the user), which can include activities, learning from within and others through choice architecture, challenges and personal messages from virtual friends, health and wealth, and rewards. The personalized micro-interventions can be individual and social learning as part of social nudging, which can include relationship between biometric parameters and lifestyle, comparing what you eat with those consumed by healthy people and people who are improving their wellness, and comparing your lifestyle with that enjoyed by healthy people and people who are improving their wellness.

In an embodiment, the personalized multimedia feedback database, which can be stored the storage device 124, is structured as follows:

$$B_1 = \begin{bmatrix} BB & CE & \text{Trigger} & \text{Context} & \text{Consumer} & G\ \& & INABC & \text{Outcomes} & \text{Utility} & \text{Feedback} \\ id & id & id & & \text{profile} & P & \text{flag} & id & \text{function} & \text{content} \end{bmatrix},$$

where BB=building block, CE=complex event, G&P=goals & preferences, and INABC=introduction, needs analysis, action plan, benefits, and concluding motivational message.

In the worst-case scenario (joint optimization), for each CE trigger id (i.e., BMI >27 and average weight loss of 2 lbs/week for a month), a total of $N_{context} \times N_{profile} \times N_{goals}$ feedback contents is needed, which can be huge. In the best-case scenario (marginal optimization), we need $N_{context}+N_{profile}+N_{goals}$, which is more manageable.

An example of a data set in the personalized multimedia feedback database is now described. The content BB matrix $B_1$ is sparse with the actual content in quotation being stored in a separate full matrix of $N_{BB}$ by 2, where $N_{BB}$ is the number of building blocks. A simple row example is as follows: 000001, convex weight trend, weight increase of $\geq 3$ sigma, {age, gender, socioeconomic status, biometric, activity/lifestyle, disease conditions, value hierarchy}, I, {exercise in 7 days, weight trend reversal in 14 days}: "I've noticed that your are beginning to gain #weight# recently after a successful weight loss program. While this may indicate that your digital scale may be shot, it also makes sense to review what can happen if the current weight trajectory continues." Any keyword surrounded by # means that the actual value from the current user database will be substituted at run time.

At most, the content BB should consist of 1 or 2 sentences consistent with the trigger event. Tailoring occurs as a function of context and user metadata. Combinatorial explosion can be minimized through a judicious combination of (a) conditional independence, (b), the sum of marginals instead of having to deal with joint distributions (conceptually similar to alternating optimization, where optimization occurs in each marginal vector space iteratively)—linear vs. exponential scaling and (c) progressive compression (one can always end at a certain point if sub-partitioning doesn't lead to improved information gain) for user metadata-based set partitioning.

In this example, trigger event={weight gain of at least 3 sigma, no activity for at least 2 weeks, no social network activity for at least 3 weeks, unfavorable biometric signals (e.g., blood pressure, cholesterol (LDL/HDL/total) and FGL), no weight loss in 2 weeks if BMI >27}; the complementary set of triggers for positive reinforcement can be included. In addition, Context={recent success but fallback, just nothing for a while, recent life events}, where recent life events={birth, death, adoption, job change/loss, move, graduation, travel for business or pleasure}.

Also in this example, user metadata={demographics, Q&A through HFA and EMA, CBM data, inferred activity and lifestyle, utility function}, where Q&A through HFA and EMA={disease states, value hierarchy, emotional state}. Moreover, INAB: Where in the message={Introduction, Needs, Action plan, Benefits, which facilitates the creation of a large number of new content by combining building blocks in the four parts of a personalized letter. This information provides clues on how to combine content BBs to create a personalized letter that has a proper content structure.

In this example, outcomes={improvement in biometrics, lifestyle change, more social interactions, improving wellness score}. Ancillary in this example includes MPAA rating (G or R, for example) or anything else that can spice up content.

Now, the level-2 and -3 content database tables look like $$B_2 = \begin{bmatrix} Para & BB \\ id & id \end{bmatrix}$$

$$B_3 = \begin{bmatrix} Msg & Para & Mutation & Outcomes \\ id & id & id & bits \end{bmatrix}$$

$$M = \begin{bmatrix} Mutation & Content \\ id & \end{bmatrix}$$

$$T = \begin{bmatrix} Trigger & Consumer \\ id & metadata \end{bmatrix}$$

This hierarchical structure is straightforward in that content BBs is first constructed using writers through a guided GUI toolkit. Two sets of content-creation business rules embedded in B2 and B3 instruct almost an infinite number of tailored messages can be created for each user over time in a context-dependent way.

The process of creating a tailored message in accordance with an embodiment of the invention is as follows. For each user, recent linked-event data is compared with a suite of business rules trigger criteria to identify opportune moments for interventions. This can be a simple duplicate-finding matrix operation involving the trigger matrix T and appended user metadata matrix. Next, for each trigger event, all the BB candidates in the matrix $B_1$ are found. Let $\Omega_i$ denote this BB candidate set for the i-th trigger. For each paragraph in $B_2$, the probability of BB match $\beta$ is computed as $$\frac{N(BB \in \Omega_i)}{N(BB \in \Omega_T)},$$

where $\Omega_T$ is the BB set for the paragraph. For example, if the paragraph contains 2 BBs in while having a total of 5 BBs in, then $\beta=0.4$. Next, paragraphs with $\beta \geq$ threshold are selected. Next, in $B_3$, all the messages with the highest average $\beta$ are found. Alternatively, a weighted score can be used using the average $\beta$ and the outcomes score, which is an indication of how effective this particular message has been for people like this user who had a similar trigger event.

In the absence of data, Occam's razor can be utilized. That is, marginal optimization and progressive tailoring to minimize the number of building blocks can be used. As more data is acquired, the hierarchical networks can be expanded only if expansion makes sense based on some criteria. This first criterion must be information gain or Kullback-Leibler divergence. The second criterion is the level of contribution to impact prediction through expansion or further partitioning. The third one is the degree of causality between different nodes in the four sets of hierarchical trees, user profile, goals and preferences, context, and KPI, as illustrated in FIG. 4.

The distinction between correlation and causation is difficult. In this case, by virtue of having temporal information and introducing the concept of state evolution over time, there is an advantage since causation generally involves a temporal dimension. Furthermore, real-time randomized controlled trials coupled with propensity-score shaping are ideal to investigate the impact of intervention while removing as many confounding factors as possible.

Besides adaptive intervention design, the AIM module 234 has a repository for complex-event (CE) trigger rules that spawn a number of processes as follows:
1. Fetch user profile, goals, preferences, and context.
2. Filter Web3 content to select appropriate content that matches the criteria dictated by the CE trigger.
3. Check the utility function associated with filtered intervention building blocks. Select the building block predicted to be most impactful for the user flagged by the current CE trigger for a given set of profile, context, goals, and preferences.
4. Stitch the selected building blocks to create a new intervention on the fly.

Figure 10:
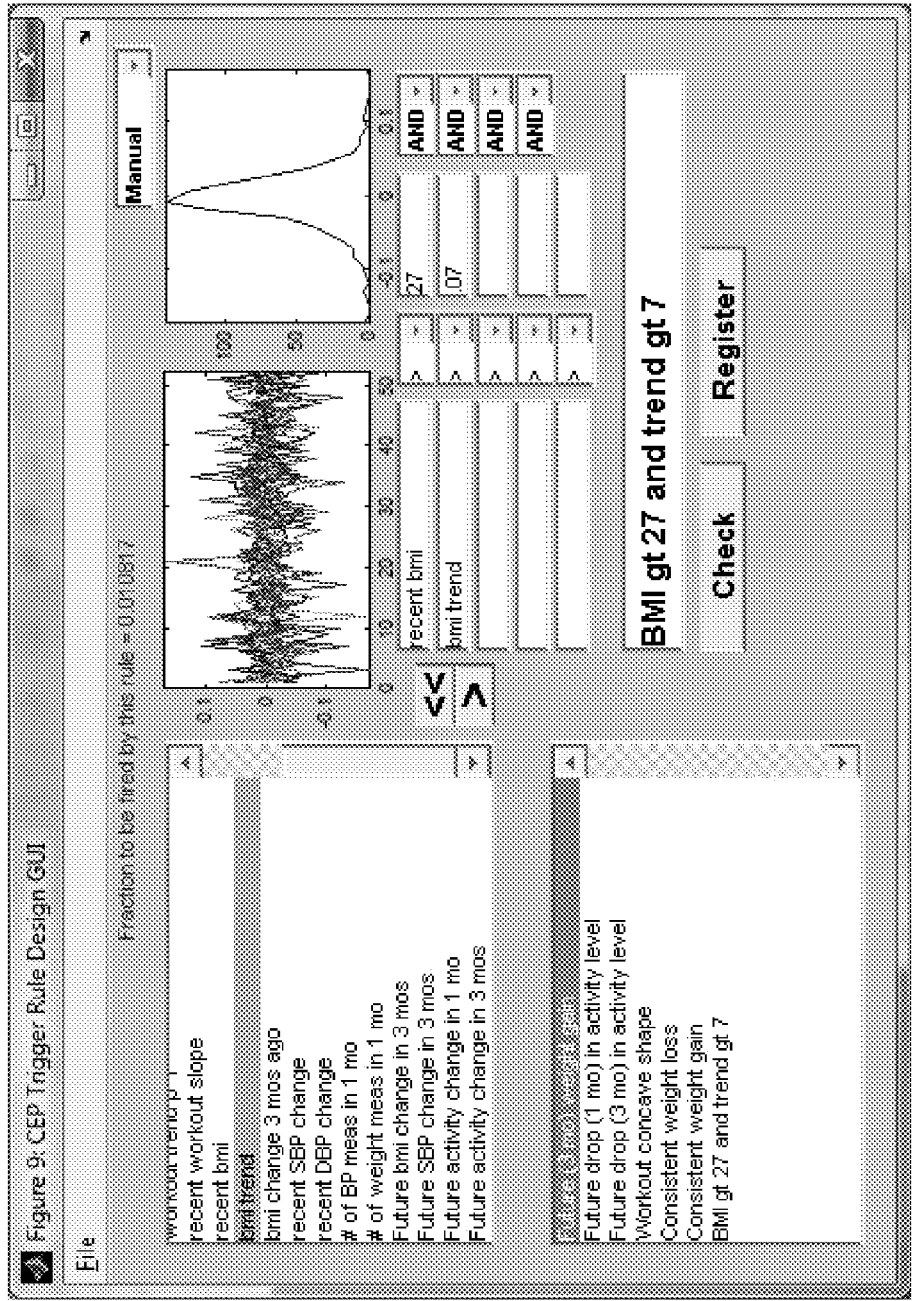
FIG. 10 illustrates a layout for building complex event trigger rules in accordance with an embodiment of the invention.

FIG. 10 shows a layout for building CE trigger rules in accordance with an embodiment of the invention. While most rules will be generated automatically from the batch analytics engine 242, this tool can be used to create CE triggers that leverage intuitions of domain experts. In this case, for example, anyone with BMI >27 and an increasing weight trend over a month will be flagged for personalized intervention. In this example, KPIs of increased activity level and decreasing weight/body fat percentage over a month can also be assigned to assess the effectiveness of the personalized intervention.

The key tenet behind automatic rules generation in the batch analytics engine 242 is to predict out-of-norm events. Instead of manually specifying "if-then-else" rules laboriously, predictive and inference models are relied on to be proactive in the intervention.

To accomplish this, a bank of predictive and inference models tailored to various population segments are built and deployed. Instead of focusing on the homogeneity of inputs, the output homogeneity is also taken into consideration so that the population clusters are generated based on the combined input-output homogeneity. In short, each user will have a small number of models running concurrently to predict various future events so that smart guidance can be provided.

Furthermore, many of these models can serve a dual purpose of teaching the user causal relationships between actions and consequences. Just as in yo-yo diet, yo-yo exercise can lead to injuries and inconsistent workout patterns. If too much exercise too fast leads to future weight gain due to the reasons cited above, the user can be asked to slow down a bit or nudge the user towards yoga or other mild exercise using a collaborative filtering-based recommendation engine. At the same time, an easy-to-understand explanation with intuitive visualization that explains the dangers of yo-yo exercise can be provided.

Figure 11:
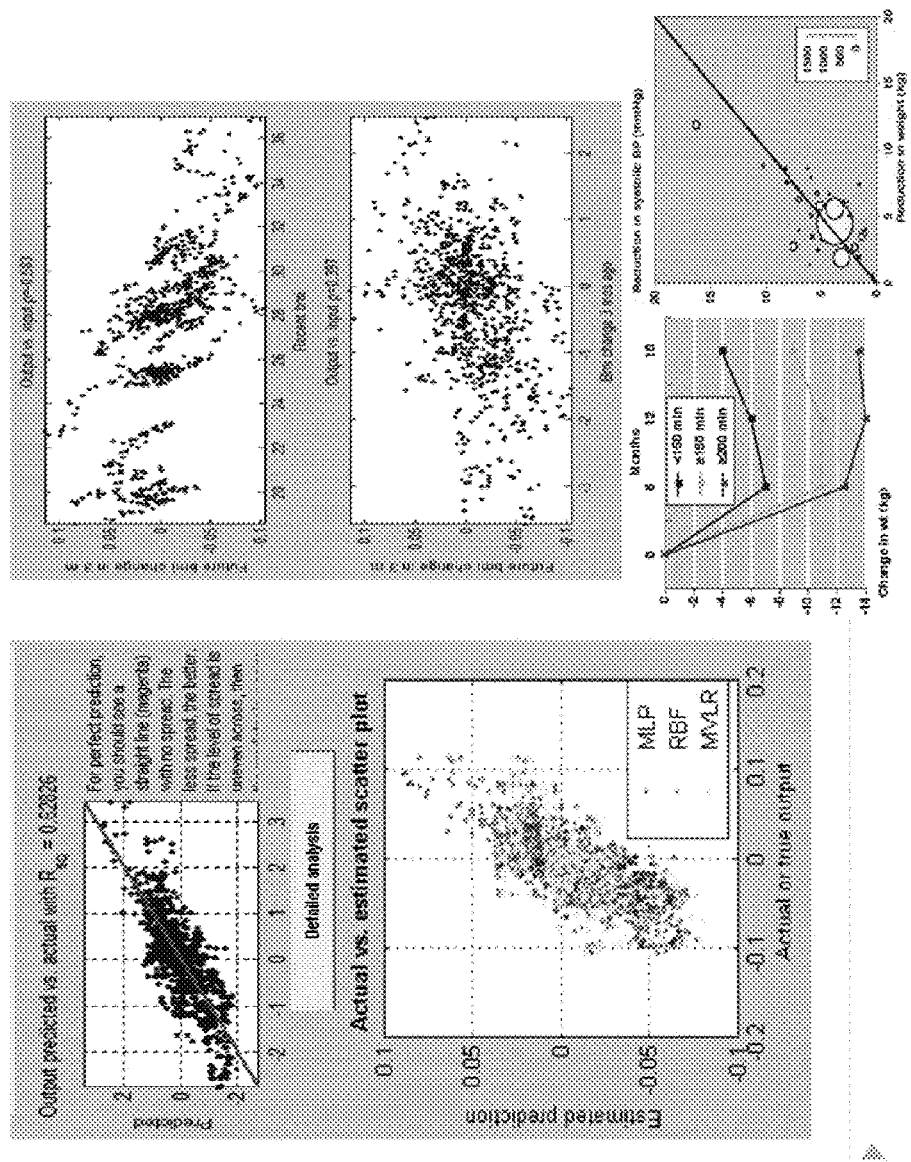
FIG. 11 illustrates several predictive models at work in accordance with an embodiment of the invention.

FIG. 11 illustrates several predictive models at work in accordance with an embodiment of the invention. In the left side of FIG. 11, three predictive models, Multi-layer Perceptron, Radial Basis Function and Multivariate Linear Regression, that are attempting to predict BMI with MLP providing the highest R-sq, are shown. In the upper right side of FIG. 11, two feature scatter plots are illustrated that show that the higher the starting BMI, the greater the weight loss and that the more one sees favorable BMI change, the more likely one is to stay the course. In the lower right side of FIG. 11, two plots chart the history of weight loss over time as a function of workout duration and show the relationship between weight loss and blood pressure.

The outcomes analytics module 234 engine is configured to perform one or more of the below-described tasks using follow-up information from users after interventions have been delivered to investigate and determine the effectiveness of the interventions. The outcomes analytics module can be configured to assign success criteria to each complex-event trigger so that the system can measure automatically the effectiveness of micro-interventions as a function of user profiles, contexts, and micro-intervention delivery methods. The outcomes analytics module can also be configured to randomly partition population for real-time randomized controlled experiments. The outcomes analytics module can also be configured to shape propensity-score of the randomly partitioned control and intervention groups for outcomes or impact difference that can be attributable to the intervention. The outcomes analytics module can also be configured to test statistical hypothesis with trend analysis to quantify the impact of intervention with further drilldown into population segments. The outcomes analytics module can also be configured to cluster interventions over time to facilitate the impact analysis of staggered interventions over time with piecewise regression so that the analysis goes beyond static intervention. The outcomes analytics module can also be configured to update the utility function for each complex-event trigger and intervention as a function of user profile, context, goals and preferences.

Figure 12:
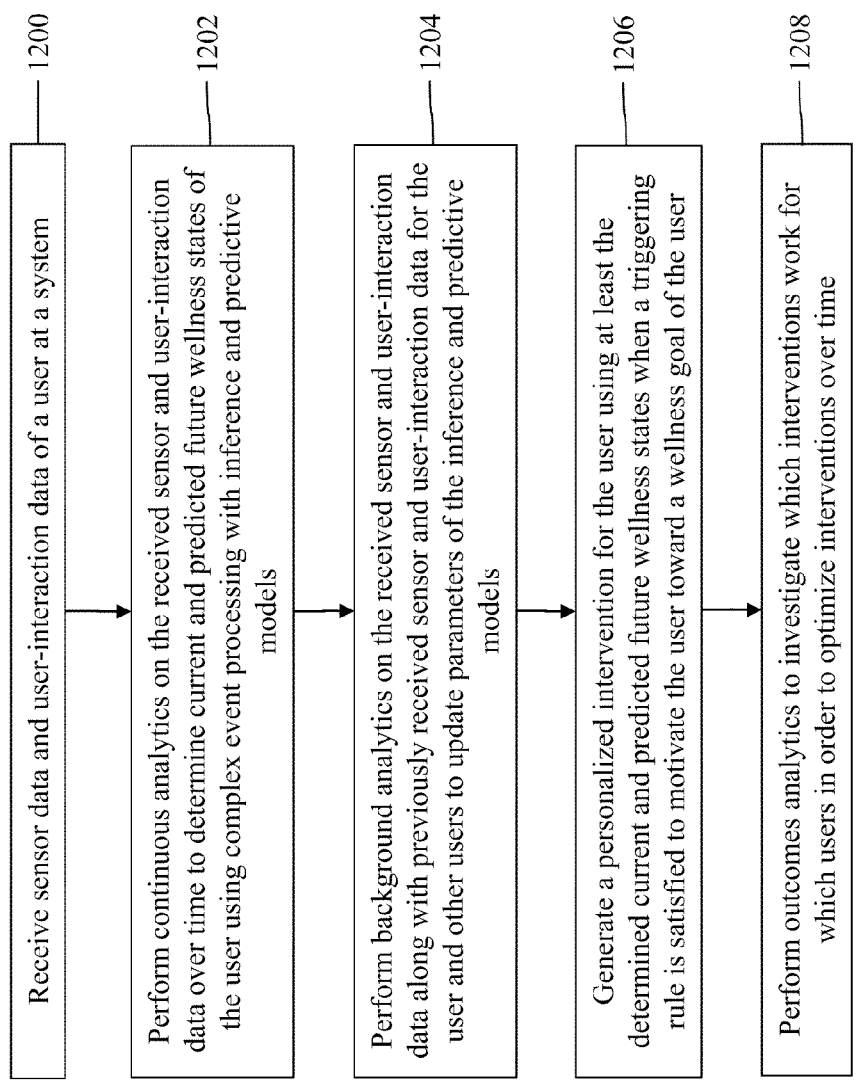
FIG. 12 is a process flow diagram of a method for motivating users to improve their wellness in accordance with an embodiment of the invention.

A method for motivating users to improve their wellness in accordance with an embodiment of the invention is described with reference to a process flow diagram of FIG. 12. At block 1200, sensor data and user-interaction data of a user are received at a system. The sensor data includes information electronically sensed from one or more sensors. The user-interaction data includes information derived from interactions between the user and the system and between the user and others in the system. At block 1202, continuous analytics is performed on the received sensor and user-interaction data over time to determine current and predicted future wellness states of the user using complex event processing with inference and predictive models. At block 1204, background analytics is performed on the received sensor and user-interaction data along with previously received sensor and user-interaction data for the user and other users to update parameters of the inference and predictive models. At block 1206, a personalized intervention is generated for the user using at least the determined current and predicted future wellness states when a triggering rule is satisfied to motivate the user toward a wellness goal of the user. At block 1208, outcomes analytics is performed to investigate which interventions work for which users in order to optimize interventions over time.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A method for motivating users to improve their wellness, the method comprising:
receiving sensor data and user-interaction data of a user at a system, the sensor data including information electronically sensed from one or more sensors, the user-interaction data including information derived from interactions between the user and the system and between the user and others in the system;
performing continuous analytics on the received sensor and user-interaction data over time to determine current and predicted future wellness states of the user using complex event processing with inference and predictive models;
performing background analytics on the received sensor and user-interaction data along with previously received sensor and user-interaction data for the user and other users to update parameters of the inference and predictive models;
generating a personalized intervention for the user using at least the determined current and predicted future wellness states when a triggering rule is satisfied to motivate the user toward a wellness goal of the user; and
performing outcomes analytics to investigate which interventions work for which users in order to optimize interventions over time.

2. The method of claim 1 wherein the sensor data includes activity data of the user and biomarker data of the user.

3. The method of claim 1 wherein the performing the background analytics includes finding relationships between user information, interventions and outcomes of the interventions, the user information including sensor and user-interaction data from the users.

4. The method of claim 1 wherein the generating the personalized intervention includes soliciting additional information from the user to improve the personalized intervention generated with respect to quality and impact.

5. The method of claim 1 wherein the performing the background analytics includes extracting contents from different sources of a communications network that are relevant to the wellness of the user, wherein at least some of the contents is used in association with the personalized intervention.

6. The method of claim 5 wherein the generating the personalized intervention includes embedding at least some of the contents into a multimedia feedback to the user to produce the personalized intervention.

7. The method of claim 1 wherein the performing the background analytics includes scoring the users with respect to social dimensions that include cultural, lifestyle and value attributes of the users.

8. The method of claim 7 wherein the generating the personalized intervention includes embedding information of others based on the scoring of these users with respect to the social dimensions into the personalized intervention.

9. The method of claim 1 wherein the performing the outcomes analytics includes updating the trigger rule as a function of profile, context, goals and preferences of the users.

10. The method of claim 1 wherein the generating the personalized intervention includes taking into consideration results from the performing the continuous analytics and the background analytics to generate the personalized intervention.

11. A system for motivating users to improve their wellness, the system comprising:
- a continuous analytics module configured to perform continuous analytics on sensor and user-interaction data of a user over time to determine current and predicted future wellness states of the user using complex event processing with inference and predictive models, the sensor data including information electronically sensed from one or more sensors, the user-interaction data including information derived from interactions between the user and the system and between the user and others in the system;
- a background analytics module configured to perform background analytics on the received sensor and user-interaction data along with previously received sensor and user-interaction data for the user and other users to update parameters of the inference and predictive models;
- an intervention module configured to generate a personalized intervention for the user using at least the determined current and predicted future wellness states when a triggering rule is satisfied to motivate the user toward a wellness goal of the user; and
- an outcomes analytics module configured to perform outcomes analytics to investigate which interventions work for which users in order to optimize interventions over time.

12. The system of claim 11 wherein the sensor data includes activity data of the user and biomarker data of the user.

13. The system of claim 11 wherein the background analytics module is configured to find relationships between user information, interventions and outcomes of the interventions, the user information including sensor and user-interaction data from the users.

14. The system of claim 11 wherein the intervention module is configured to solicit additional information from the user to improve the personalized intervention generated with respect to quality and impact.

15. The system of claim 11 wherein the background analytics module is configured to extract contents from different sources of a communications network that are relevant to the wellness of the user, wherein at least some of the contents is used in association with the personalized intervention.

16. The system of claim 15 wherein the intervention module is configured to embed at least some of the contents into a multimedia feedback to the user to produce the personalized intervention.

17. The system of claim 11 wherein the background analytics module is configured to score the users with respect to social dimensions that include cultural, lifestyle and value attributes of the users.

18. The system of claim 17 wherein the intervention module is configured to embed information of others based on the scoring of these users with respect to the social dimensions into the personalized intervention.

19. The system of claim 11 wherein the outcomes analytics module is configured to update the trigger rule as a function of profile, context, goals and preferences of the users.

20. The system of claim 11 wherein the intervention module is configured to take into consideration results from the continuous analytics module and the background analytics module to generate the personalized intervention.

* * * * *